US009045718B2

(12) United States Patent
Hubrig

(10) Patent No.: US 9,045,718 B2
(45) Date of Patent: Jun. 2, 2015

(54) RESIDUE CLEANING COMPOSITION AND METHOD

(71) Applicant: Innovation Services, Inc., Knoxville, TN (US)

(72) Inventor: Jeffrey G. Hubrig, Knoxville, TN (US)

(73) Assignee: Innovation Services, Inc., Knoxville, TN (US)

( * ) Notice: Subject to any disclaimer, the term of this patent is extended or adjusted under 35 U.S.C. 154(b) by 0 days.

(21) Appl. No.: 14/050,704

(22) Filed: Oct. 10, 2013

(65) Prior Publication Data

US 2014/0034089 A1 Feb. 6, 2014

Related U.S. Application Data

(63) Continuation-in-part of application No. 13/946,625, filed on Jul. 19, 2013, which is a continuation-in-part of application No. 12/869,183, filed on Aug. 26, 2010, which is a continuation-in-part of application No. 11/697,933, filed on Apr. 9, 2007, now Pat. No. 7,799,234, and a continuation-in-part of application No. 11/697,921, filed on Apr. 9, 2007, now Pat. No. 7,794,606.

(51) Int. Cl.
C11D 3/48 (2006.01)
C11D 3/34 (2006.01)
C11D 1/66 (2006.01)
A61L 11/00 (2006.01)
B09B 3/00 (2006.01)
A61L 2/18 (2006.01)
A61L 2/22 (2006.01)
C11D 11/00 (2006.01)

(52) U.S. Cl.
CPC ............... C11D 3/3409 (2013.01); C11D 1/66 (2013.01); *C11D 11/0023* (2013.01); *C11D 3/48* (2013.01); *C11D 11/0011* (2013.01); *C11D 11/0041* (2013.01); A61L 11/00 (2013.01); *B09B 3/0075* (2013.01); B09B 3/0091 (2013.01); A61L 2/18 (2013.01); A61L 2/22 (2013.01); *A61L 2202/17* (2013.01); *A61L 2202/24* (2013.01)

(58) Field of Classification Search
CPC .. C11D 3/48; C11D 11/0011; C11D 11/0023; C11D 11/0041
USPC ............................................ 510/161; 134/26
See application file for complete search history.

(56) References Cited

U.S. PATENT DOCUMENTS

| 2,243,761 | A |   | 5/1941  | Matzka            |        |
|-----------|---|---|---------|-------------------|--------|
| 2,658,033 | A |   | 11/1953 | Ferris            |        |
| 2,687,996 | A |   | 8/1954  | Butler            |        |
| 3,703,453 | A |   | 11/1972 | Gordy et al.      |        |
| 3,864,258 | A |   | 2/1975  | Richardson et al. |        |
| 3,925,176 | A |   | 12/1975 | Okert             |        |
| 4,054,139 | A |   | 10/1977 | Crossley          |        |
| 4,174,280 | A |   | 11/1979 | Pradt et al.      |        |
| 4,179,347 | A |   | 12/1979 | Krause et al.     |        |
| 4,192,742 | A |   | 3/1980  | Bernard et al.    |        |
| 4,197,347 | A |   | 4/1980  | Ogawa et al.      |        |
| 4,273,884 | A |   | 6/1981  | Dominguez         |        |
| 4,292,175 | A |   | 9/1981  | Krase et al.      |        |
| 4,492,618 | A |   | 1/1985  | Eder              |        |
| 4,680,114 | A |   | 7/1987  | Hayes             |        |
| 4,741,831 | A |   | 5/1988  | Grinstead         |        |
| 4,783,246 | A |   | 11/1988 | Langeland et al.  |        |
| 4,784,790 | A | * | 11/1988 | Disch et al. ..................... | 422/20 |
| 4,935,116 | A |   | 6/1990  | LeMire            |        |
| 4,992,213 | A |   | 2/1991  | Mallett et al.    |        |
| 4,994,200 | A | * | 2/1991  | Disch et al. .................. | 510/161 |
| 5,059,296 | A |   | 10/1991 | Sherman           |        |
| 5,073,298 | A |   | 12/1991 | Gentle et al.     |        |
| 5,073,382 | A |   | 12/1991 | Antelman          |        |
| 5,077,007 | A |   | 12/1991 | Pearson           |        |
| 5,078,902 | A |   | 1/1992  | Antelman          |        |
| 5,085,753 | A |   | 2/1992  | Sherman           |        |
| 5,087,370 | A |   | 2/1992  | Schultheis et al. |        |
| 5,094,739 | A |   | 3/1992  | Kump              |        |
| 5,149,354 | A |   | 9/1992  | Delaney           |        |
| 5,223,166 | A | * | 6/1993  | Disch et al. .................. | 514/693 |
| 5,228,964 | A |   | 7/1993  | Middleby          |        |

(Continued)

FOREIGN PATENT DOCUMENTS

| DE | 10009643 | 9/2001 |
| GB | 384466   | 12/1932 |

(Continued)

OTHER PUBLICATIONS

I.B. Romans, Oligodynamic Metals, Disinfection, Sterilization, and Preservation, 1968, Chapter 24, 372-400, Lea & Febiger, Philadelphia.
I.B. Romans, Silver Compounds, Disinfection, Sterilization, and Preservation, 1968, Chapter 28, 469-474, Lea & Febiger, Philadelphia.
John G. Dean et al., Heavy Metals from Waste Water, Environmental Science & Technology, Jun. 1972, 519-522, vol. 6, No. 6.
Silver, Nature's Water Purifier, www.doulton.ca/silver.html., Feb. 27, 1997, 1-6.
Tests Show Silver Best "Swimming Pool" Water Purifier, the Silver Institute Letter, May 1975, vol. VI, No. 11.
J. O. Noyce et al., Use of Copper Cast Alloys to Control *Escherichia coli* O157 Cross-Contamination During Food Processing, Applied and Environmental Microbiology, Jun. 2006, 4239-4244, vol. 72, No. 6.
H.T. Michels et al., Copper Alloys for Human Infectious Disease Control, Materials Science and Technology Conference, Sep. 25-28, 2005, Pittsburg, PA.
Dual Sanitation with Copper Silver Ion, Ideal Distributors Limited, 2007, 1-4.
John Apsley et al., Nanotechnology's Latest Oncolytic Agent: Silver, Cancer, & Infection Associations, Townsend Letter for Doctors and Patients, May 2006.

(Continued)

*Primary Examiner* — Gregory Webb
(74) *Attorney, Agent, or Firm* — Leudeka Neely Group, P.C.

(57) ABSTRACT

A medical surface cleaning composition and a method for cleaning waste treatment system components, medical instruments surfaces, and enzyme residue-containing surfaces. The composition includes a residue cleaning agent and a substantially non-water soluble nonionic surfactant having an initial Ross-Miles foam height in an aqueous solution at 25° C. of less than 10 millimeters. A weight ratio of residue cleaning agent to surfactant on 100 wt. % active ingredient basis ranges from about 0.05:1 to about 0.5:1, and wherein the residue cleaning agent and surfactant are biodegradable.

10 Claims, No Drawings

(56) References Cited

U.S. PATENT DOCUMENTS

| | | | |
|---|---|---|---|
| 5,234,832 A * | 8/1993 | Disch et al. | 435/264 |
| 5,248,486 A | 9/1993 | Matsuoka et al. | |
| 5,324,434 A | 6/1994 | Oikawa et al. | |
| 5,346,627 A | 9/1994 | Siefert et al. | |
| 5,364,512 A | 11/1994 | Earl | |
| 5,387,350 A | 2/1995 | Mason | |
| 5,454,953 A | 10/1995 | Waibel | |
| 5,476,579 A | 12/1995 | Choi et al. | |
| 5,492,633 A | 2/1996 | Moniwa et al. | |
| 5,531,865 A | 7/1996 | Cole | |
| 5,543,040 A | 8/1996 | Fite, Jr. et al. | |
| 5,688,981 A | 11/1997 | Nonomura | |
| 5,753,100 A | 5/1998 | Lumsden | |
| 5,759,384 A | 6/1998 | Silveri | |
| 5,772,896 A | 6/1998 | Denkewicz, Jr. et al. | |
| 5,783,090 A | 7/1998 | Gleen | |
| 5,820,541 A | 10/1998 | Berlanga Barrera | |
| 5,820,761 A | 10/1998 | Holzer et al. | |
| 5,858,246 A | 1/1999 | Rafter et al. | |
| 5,858,256 A | 1/1999 | Minne et al. | |
| 5,885,426 A | 3/1999 | Silveri | |
| 5,919,367 A | 7/1999 | Khudenko | |
| 5,938,900 A | 8/1999 | Reynolds | |
| 5,944,973 A | 8/1999 | Hall | |
| 5,958,252 A | 9/1999 | Shades | |
| 6,017,461 A | 1/2000 | Garvey et al. | |
| 6,093,422 A | 7/2000 | Denkewicz, Jr. et al. | |
| 6,096,219 A | 8/2000 | Green et al. | |
| 6,113,779 A | 9/2000 | Snee | |
| 6,126,830 A | 10/2000 | Marshall | |
| 6,149,821 A | 11/2000 | Rounds et al. | |
| 6,197,814 B1 | 3/2001 | Arata | |
| 6,210,078 B1 | 4/2001 | Redwine et al. | |
| 6,270,650 B1 | 8/2001 | Kazi et al. | |
| 6,287,450 B1 | 9/2001 | Hradil | |
| 6,346,627 B1 | 2/2002 | Liotta et al. | |
| 6,358,395 B1 | 3/2002 | Schorzman et al. | |
| 6,448,062 B1 * | 9/2002 | Huth et al. | 435/264 |
| 6,495,052 B1 | 12/2002 | Miyamoto et al. | |
| 6,514,406 B1 | 2/2003 | Katehis | |
| 6,521,131 B1 | 2/2003 | Hamilton et al. | |
| 6,746,593 B2 | 6/2004 | Herbst | |
| 6,780,306 B2 | 8/2004 | Schlager et al. | |
| 6,783,679 B1 | 8/2004 | Rozich | |
| 6,855,678 B2 * | 2/2005 | Whiteley | 510/161 |
| 7,056,061 B2 | 6/2006 | Kukor et al. | |
| 7,198,680 B1 | 4/2007 | Dooley et al. | |
| 7,238,287 B2 | 7/2007 | Kulperger | |
| 7,387,719 B2 | 6/2008 | Carson et al. | |
| 7,691,251 B2 | 4/2010 | Carson et al. | |
| 8,420,584 B2 * | 4/2013 | Thoele et al. | 510/161 |
| 2002/0144958 A1 | 10/2002 | Sherman | |
| 2002/0155044 A1 | 10/2002 | Ciampi et al. | |
| 2002/0157962 A1 | 10/2002 | Robey et al. | |
| 2003/0100101 A1 * | 5/2003 | Huth et al. | 435/264 |
| 2003/0132172 A1 | 7/2003 | Hayes | |
| 2003/0161758 A1 * | 8/2003 | Whiteley | 422/28 |
| 2005/0034978 A1 | 2/2005 | Kazi et al. | |
| 2005/0199557 A1 | 9/2005 | Johnston et al. | |
| 2006/0000784 A1 | 1/2006 | Khudenko | |
| 2006/0043011 A1 | 3/2006 | King et al. | |
| 2006/0125396 A1 | 6/2006 | Han et al. | |
| 2006/0175266 A1 | 8/2006 | Rima et al. | |
| 2007/0179071 A1 * | 8/2007 | Thoele | 510/161 |
| 2008/0245744 A1 | 10/2008 | Dooley et al. | |
| 2009/0203565 A1 * | 8/2009 | Dooley et al. | 510/161 |
| 2010/0075883 A1 * | 3/2010 | Geret et al. | 510/161 |
| 2010/0249005 A1 * | 9/2010 | Thoele et al. | 510/161 |
| 2011/0104373 A1 * | 5/2011 | Dooley et al. | 427/307 |
| 2012/0172271 A1 * | 7/2012 | Hubrig et al. | 510/161 |
| 2012/0234357 A1 | 9/2012 | Labib et al. | |

FOREIGN PATENT DOCUMENTS

| | | |
|---|---|---|
| GB | 1400215 | 7/1975 |
| GB | 2298858 | 9/1996 |
| JP | 11235597 | 8/1999 |
| JP | 2003039083 | 2/2003 |
| WO | 9918790 | 4/1999 |
| WO | 0236499 | 5/2002 |
| WO | 2006065825 | 6/2006 |
| WO | 2008124299 | 10/2008 |

OTHER PUBLICATIONS

F. X. Abad et al., Disinfection of Human Enteric Viruses in Water by Copper and Silver in Combination with Low Levels of Chlorine, Applied and Environmental Microbiology, Jul. 1994, 2377-2383, vol. 60, No. 7.

Charles F. McKhann, M.D. et al., Oligodynamic Action of Metallic Elements and of Metal Alloys on Certain Bacteria and Viruses, Dec. 1985, 95-101, vol. 182(1).

M.T. Yahya et al., Disinfection of Bacteria in Water Systems by Using Electrolytically Generated Copper: Silver & Reduced Levels of Free Chlorine, Canadian Journal of Microbiology, 1990, 109-116, vol. 36.

H. Akiyama, Prophylaxis of Indwelling Urethral Catheter Infection: Clinical Experience with a Modified Foley Catheter and Drainage System, The Journal of Urology, 1979, 40-42, vol. 121.

Janet E. Stout, Experiences of the First 16 Hospitals Using Copper-Silver Ionization for Legionella Control: Implications for the Evaluation of Other Disinfection Modalities, Infection Control and Hospital Epidemiology, Aug. 2003, 1-6, vol. 24, No. 8.

J. A. Spardo et al., Antibacterial Effects of Silver Electrodes with Weak Direct Current, Antimicrobial Agents and Chemotherapy, Nov. 1974, 637-642, vol. 6, No. 5.

Lee K. Landeen, Efficacy of Copper and Silver ions and Reduced Levels of Free Chlorine in Inactivation of *Legionella pneumophila*, Applied and Environmental Microbiology, Dec. 1989, 3045-3050, vol. 55, No. 12.

Robert Niven, Investigation of Silver Electrochemistry Water Disinfection Applications, CIVE 651: Principles of Water and Wastewater Treatment, McGill University, Apr. 13, 2005.

Leonard Zimmerman, Toxicity of Copper and Ascorbic Acid to *Serratia marcescens*, Journal of Bacteriology, Apr. 1966, 1537-1542, vol. 91, No. 4.

Oligodynamic Ag: The Active Ingredient in Sovereign Silver and Argentyn 23, Natural-Immunogenics Corp.

William H. Dresher, Copper Helps Control Deadly Prion Protein Infection, Innovations in Copper, Oct. 2006, 1-4.

Andrew A. Marino, Electrochemical Propoerties of Silver-Nylon Fabrics, Journal of the Electrochemical Society, Electrochemical Science and Technology, Jan. 1985, 68-72, vol. 132, No. 1.

C.P. Davis, Iontophoretic Killing of *Escherichia coli* in Static Fluid and in a Model Catheter System, Journal of Clinical Microbiology, May 1982, 891-894, vol. 15, No. 5.

Q. L. Feng et al., A Mechanistic Study of the Antibacterial Effect of Silver Ions on *Escherichia coli* and *Staphylococcus aureus*, Journal of Biomedical Materials, 2000, 662-668, vol. 52.

Studies and Published Papers on Ionisation, Copper, Chlorine Efficacy and Related Issues, http://www.ecosmarte.com.au, Mar. 13, 2007, 1-95.

J. M. Cassells et al., Efficacy of a Combined System of Copper and Silver and Free Chlorine for Inactivation of *Naegleria fowleri* Ameobas in Water, Water Science and Technology, 1995, 119-122, vol. 31, No. 5-6.

R. R. Khaydarov et al., Water Disinfection Using Silver and Copper Ions and Collodial Gold, Modern Tools and Methods of Water Treatment for Improving Living Standards, 2005, 159-166, Netherlands.

X. Y. Li et al., Electrochemical Wastewater Disinfection: Identification of Its Principal Germicidal Actions, Journal of Environmental Engineering, Oct. 2004, 1217-1221.

X. Y. Li et al., Electrochemical Disinfection of Saline Wastewater Effluent, Journal of Environmental Engineering, Aug. 2002, 697-704.

"Defoaming Surfactants," a bulletin from the Dow Chemical Company, Midland, Michigan 48674, Form. No. 119-02159-0306 AMS.

* cited by examiner

RESIDUE CLEANING COMPOSITION AND METHOD

RELATED APPLICATIONS

This application is a continuation-in-part of application Ser. No. 13/946,625, filed Jul. 19, 2013, which is a continuation-in-part of co-pending application Ser. No. 12/869,183, filed Aug. 26, 2010, which is a continuation-in-part of U.S. Pat. No. 7,799,234 issued Sep. 21, 2010 and U.S. Pat. No. 7,794,606 issued Sep. 14, 2010.

FIELD OF THE DISCLOSURE

The present disclosure is generally directed toward compositions and methods for removing enzymatic cleaner residues and residual films from metallic and non-metallic surfaces of a medical waste treatment system or metallic and non-metallic surfaces that have come in contact with biological and/or pharmaceutical components from a medical or surgical procedure. The enzymatic cleaner residues and residual films typically result from cleaning and rinsing the metallic and non-metallic surfaces that have been in contact with the biological and/or pharmaceutical components. More specifically, the compositions and methods of the present disclosure are directed to compositions for use in hospitals and other medical facilities for removing residual traces of cleaning agents from surgical fluid medical waste treatment system surfaces, collection system surfaces, medical instruments and/or any other hard surfaces that have been initially cleaned and/or rinsed with enzymatic cleaners and other commercial cleaning compositions.

BACKGROUND AND SUMMARY

Hospitals, surgery centers and other medical treatment facilities use a variety surgical and medical instruments and devices that must be cleaned, disinfected, and reused. Such facilities have established a large number of commercially available and commonly employed cleaning agents that can leave trace amounts of the cleaning agent behind on the cleaned surface following a rinse cycle. While trace amounts of cleaning agent residuals, associated most notably with enzymatic cleaners, are within acceptable limits for washing, rinsing, disinfecting and sterilizing of surgical, medical and other devices, the residual components of such cleaning agents represent a surface contamination that may interfere with the functionality of surgical instruments and with the functionality and efficacy of components within a waste treatment system used by the same hospitals, surgery centers and other medical treatment facilities. Common practice within such facilities leads to the use of manual and automatic washer cleaning agents to clean waste treatment systems and other hard surfaces with a corresponding loss of efficacy and service life performance from critical component contamination caused by the trace amounts of cleaning agent residues.

In large medical facilities, surgical and medical instruments and devices are collected in a central location and are washed by hand and/or in an automatic washing machine before being sterilized and repackaged in a sterile container for reuse by medical personnel. Other devices that must be decontaminated may include waste collection systems and other devices that come in contact with bodily fluids and surgical waste streams.

Cleaning, not sterilization (or disinfection), is a first and most important step in any medical instrument processing protocol. Without first subjecting the instruments to a thorough, validated and standardized (and ideally automated) cleaning process, the likelihood that any disinfection or sterilization process will be effective is significantly reduced.

An automated washer/disinfector cleans and decontaminates dirty medical surgical instruments so they can be handled safely, repackaged, and sterilized for a future surgery. The danger of handling instruments contaminated with blood is obvious in this age of hepatitis, CJD and HIV. The procedures for sterilizing medical instruments are based on years of scientific testing of cleaning instruments. If surgical instruments are not clean, the procedures are ineffective. Dried blood on instruments is hazardous to the employees of the hospital and to the next surgical patient upon which the instruments are used.

Cleaning dried blood is much more difficult than cleaning dirt. Blood coagulates, which means it goes from a free-flowing liquid to a solid that contains tough, microscopic fibers called fibrin. These fibers form as the blood coagulates and jam themselves into microscopic irregularities in the surface of the stainless steel instrument. There is a physical attachment of the fibers to the surface through mechanical means, not chemical means as with traditional adhesives. The action is similar to the roots of plants growing into cracks in rocks, anchoring themselves to the surface.

Another factor that makes blood difficult to clean is its ability to become insoluble when heated. Heating causes blood to denature. Denaturing is similar to what happens to eggs cooked in a frying pan. Transparent uncooked egg whites are fairly easy to wash away, but opaque, cooked egg whites are much more difficult to remove from surfaces. Dried, uncooked egg is even more difficult to wash away, as is dried blood, the proteins in blood are similar to albumin proteins in eggs.

Current automatic washing machines are designed to use a variety of enzyme-based cleaning compositions. However, the enzyme-based cleaning compositions must be used under tightly controlled conditions in order to effectively clean and/or disinfect the medical instruments and devices. Often, the enzyme cleaning compositions leave residual enzyme components on the instruments and devices causing a need to re-clean the instruments and devices before they are reused. Also, the enzyme cleaning compositions are not always effective for cleaning hard to reach surfaces of the medical devices and instruments, if the enzyme residue is allowed to remain on the surfaces of the instruments, the enzyme residual may cause premature failure of the instruments. Accordingly, there is a need for improved cleaning compositions for use in cleaning medical instruments and enzyme residue-containing surfaces.

With regard to the foregoing needs, the disclosure provides a medical surface cleaning composition and a method for cleaning waste treatment system components, medical instrument surfaces, and enzyme residue-containing surfaces. The composition includes a residue cleaning agent and a substantially non-water soluble nonionic surfactant having an initial Ross-Miles foam height in an aqueous solution at 25° C. of less than 10 millimeters. A weight ratio of residue cleaner to surfactant on 100 wt. % active ingredient basis ranges from about 0.05:1 to about 0.5:1. The residue cleaning agent and surfactant are biodegradable.

Another embodiment of the disclosure provides a method for cleaning waste treatment system components, medical instruments surfaces, and enzyme residue-containing surfaces. The method includes applying to a surface to be cleaned a composition that includes a residue cleaning agent and a substantially non-water soluble nonionic surfactant having an initial Ross-Miles foam height in an aqueous solution at 25° C. of less than 10 millimeters. A weight ratio of residue cleaning agent to surfactant on 100 wt. % active ingredient basis ranges from about 0.05:1 to about 0.5:1. An amount of composition is sprayed onto the surface that is sufficient to effectively clean and remove residue from the surface. The surface is then rinsed with purified water to remove the composition from the cleaned surface.

An embodiment of the disclosure also includes a method for removing enzyme residue from enzyme residue-containing surfaces. The method includes applying to a surface to be cleaned a composition that includes a residue cleaning agent and a substantially non-water soluble nonionic surfactant having an initial Ross-Miles foam height in an aqueous solution at 25° C. of less than 10 millimeters. A weight ratio of residue cleaning agent to surfactant on 100 wt. % active ingredient basis ranges from about 0.05:1 to about 0.5:1. An amount of composition is sprayed onto the surface that is sufficient to effectively clean and remove residue from the surface. The surface is then rinsed with purified water to remove the composition from the cleaned surface.

Yet another embodiment of the disclosure provides a method cleaning a medical waste treatment system to remove residue and film formation on surfaces of the medical waste treatment system. The method includes injecting into the waste treatment system a composition that includes a residue cleaning agent and a substantially non-water soluble nonionic surfactant having an initial Ross-Miles foam height in an aqueous solution at 25" C. of less than 10 millimeters. A weight ratio of residue cleaning agent to surfactant in the composition on 100 wt. % active ingredient basis ranges from about 0.05:1 to about 0.5:1. The amount of composition injected into the waste treatment system is sufficient to effectively clean and remove residue from surfaces of the medical waste treatment system. Subsequent to cleaning, the surfaces of the system are rinsed with purified water to remove the composition from the cleaned surfaces.

An advantage of the compositions and methods described herein is that the compositions are not highly corrosive, are low-foaming, and do not rely on the use of enzymatic agents. Enzymatic agents are highly sensitive to alkaline or acid components used in conventional cleaning compositions and to water temperatures. Another disadvantage of enzymatic cleaning agents is that such agents typically leave an enzyme cleaner residue on the cleaned surfaces that can build up over time and cause premature failure of sensitive waste treatment system components and/or medical instruments. The compositions described herein require only a single, substantially non water soluble, non-ionic surfactant and are effective for removing residual enzyme cleaner residues from the surfaces of medical instruments and other devices that were previously cleaned with enzyme cleaning agents.

Another advantage of the compositions and methods described herein is that the compositions leave substantially no detectible residue on the cleaned surfaces. A surface having no detectible residue is a surface that is visually clean to the naked eye and, over time, has no visible build up of residue upon subsequent cleaning with the same cleaning composition.

Another advantage of the compositions described here is that the compositions are optically clear and concentrates of the composition are stable over time, i.e., do not form visible precipitates in an aqueous solution of the concentrate, despite the use of a substantially non-water soluble surfactant. A further advantage of the compositions described, herein is that the compositions have low or no foaming tendencies thereby enabling the compositions to effectively wet the surfaces to be cleaned without interference of foam adjacent to the surfaces. The low foaming tendency of the compositions make the compositions suitable for spray application to the surfaces under turbulent flow conditions. Other advantages may be apparent from the following detailed description.

DETAILED DESCRIPTION OF EXEMPLARY EMBODIMENTS

For the purposes of this disclosure, the compositions described herein are made from biodegradable components. Such biodegradable components include organic compounds that are devoid of aromatic and beretocyclic groups. Accordingly, a first component of the compositions described herein is a residue cleaning agent that is provided by a biodegradable compound.

The residue cleaning agent is typically provided as a 30 wt. % solution of active ingredient. By "active ingredient" is meant the chemical compound is dissolved in a suitable solvent in order to provide the residue agent. Other solutions may be used that contain from 10 to about 50 wt. % or more of active ingredient. Accordingly, various aspects of the compositions will be discussed in terms of 100 wt. % active ingredients since the concentration of the residue cleaning agent in the cleaning composition concentrate may vary depending on the source of the residue cleaning agent.

Suitable residue cleaning agents may be selected from alkyl ether sulfates. Alkyl ether sulfates that may be used, include but are not limited, to, sodium coconut alkyl sulfate, potassium coconut alkyl sulfate, potassium lauryl sulfate, sodium lauryl sulfate, sodium yellow fatty alcohol ether sulfate, tallow fatty alcohol sulfate (25 ethylene oxide), tallow fatty ether sulfate, sodium dodecyl benzene sulfonate, sodium stearyl sulfate, sodium palmityl sulfate, sodium decyl sulfate, sodium myristyl sulfate, sodium dodecyl sulfate, potassium dodecyl benzene sulfonate, potassium stearyl sulfate, potassium palmityl sulfate, potassium decyl sulfate, potassium myristyl sulfate, potassium dodecyl sulfate, and mixtures thereof.

Other examples of residue cleaning agents that may be used are sodium lauryl ether sulfate, ammonium lauryl sulfate, ammonium lauryl ether sulfate, sophorose biosurfactant, sodium lauroyl sarcosinate, triethanolamine lauroyl-L-glutarnate, sodium myristyl sarcosinate, potassium laurate, sodium dodecane sulfonates, and sodium lauryl ethoxysulfate.

Without desiring to be bound by theoretical considerations, it is believed, that the residue cleaning agent in the composition may react with lipid, protein, and/or enzyme residues on a surface of the medical instruments and devices to begin breaking down and denaturing both lipid, and protein complexes and enzyme residues present on the surfaces of the instruments and devices. The residue cleaning agent may also interact with a bio-film layer on the surfaces of the instruments and devices through absorption and permeation to induce molecular cleavage within the bio-film structure so as to initiate adhesive failure at a boundary layer between the bio-film structure and the underlying substrate surface. Once adhesion failure is induced by the residue cleaning agent, the organic material on the surfaces of the instruments and devices may be readily rinsed from the instruments and devices with plain water.

A particularly useful residue cleaning agent for use in the compositions described herein is sodium lauryl sulfate (SLS). SLS is often referred to as an anionic surfactant. However, in the compositions described herein, SLS has more of a detergent effect. The compositions described herein may contain an amount of SLS, on an active ingredient basis, that is effective to promote permeation, solubilization and mobilization of protein, lipid structures, and/or enzyme residues, thereby releasing the bio-film and enzyme residues from surface of the devices and instruments. Accordingly, the amount of residue cleaning agent in the washing solutions described herein may range from 5 mL per liter of total washing liquid to about 150 mL per liter of total washing liquid based on a 30 wt. % active solution of residue cleaning agent.

The second important component of the compositions described herein is a nonionic, non-water soluble surfactant having an initial Ross-Miles foam height in an aqueous solution at 25° C. of less than 10 millimeters, such as less than about 7 millimeters, or less than about 5 millimeters, and desirably less than about 3 millimeters. The Ross-Miles foam height of a compound is determined according to ASTM D1173 using a 0.1 wt. % aqueous solution of the compound at a temperature of 25° C.

The nonionic surfactants which may be used may be selected from biodegradable, linear and branched alkoxylated alcohols. Still further illustrative examples of nonionic surfactants include primary and, secondary linear and branched alcohol ethoxylates, such as those based on $C_6$ to $C_{18}$ alcohols which further include an average of from 1 to 80 moles of ethoxylation per mol of alcohol.

Further examples of useful nonionic surfactants include secondary $C_{12}$ to $C_{18}$ alcohol ethoxylates, including those which have from about 3 to about 10 moles of ethoxylation. Further exemplary nonionic surfactants include linear primary $C_{11}$ to $C_{15}$ alcohol ethoxylates, including those which have from about 3 to about 10 moles of ethoxylation. Other surfactants include linear $C_{11}$ alcohol with 1 mole (average) of ethylene oxide. Examples include polyoxyethylene (2) cetylether and polyoxyetylene (2) oleylether.

Other examples of useful nonionic surfactants include polyethylene-block poly(ethylene glycol) surfactants having an number average molecular weight of about 875; and poly (ethylene glycol)-block poly(propylene glycol)-block-polyethylene glycol) copolymers having number average molecular weights ranging from about 1100 to about 3500.

Still other non-ionic surfactants which may be used include: fatty acid monoalkylolamide ethoxylates, fatty amine alkoxylates and fatty acid glyceryl ester ethoxylates. Other non-ionic compounds suitable for inclusion in compositions of the disclosed embodiments include mixed ethylene oxide propylene oxide block copolymers, low relative molecular mass polyethylene glycols, ethylene glycol monoesters, amine oxides and alkyl polyglycosides, alkyl sugar esters including alkyl sucrose esters and alkyl oligosaccharide ester, alkyl capped polyvinyl alcohol and alkyl capped polyvinyl pyrrolidone.

Of the foregoing nonionic surfactants, one or more ethoxylated linear or branched alcohol nonionic surfactants having an initial Ross-Miles foam height of a 0.1 wt % aqueous solution at 25° C. ranging from about 1 to less than about 10 millimeters, such as from 2 to less than about 7 millimeters, and particularly from about 2 to less than about 5 millimeters may provide the most suitable foam inhibiting effects in combination with the residue cleaning agent. Accordingly, the surfactant may be a single surfactant with an initial Ross-Miles foam height of a 0.1 wt % aqueous solution 25° C. of less than 10 millimeters, or a combination of surfactants having the same initial Ross-Miles foam height. The amount of nonionic surfactant relative to the amount of residue cleaning agent on a weight ratio basis (100 wt. % active ingredient) in the compositions described herein may range from about 2:1 to about 20:1. For example, cleaning composition concentrates may include a weight ratio of surfactant to residue cleaning agent of from about 3:1 to about 8:1 or from about 4:1 to about 6:1. For the purposes of this disclosure, all references to the nonionic surfactant is with respect to a surfactant that is 100 wt. % active ingredient.

An optional component of the compositions described herein is an aqueous solvent, such as water. Washing solution concentrates as described herein may typically contain a major amount of water. Accordingly, the compositions may contain from about 50 to about 99.9 volume percent water. For example, the compositions from about 60 to about 95 volume percent water. Other compositions may include from about 75 to about 90 volume percent water. Solubilizing agents may be included in the compositions to aid in solubilizing the components of the composition. For example, concentrates containing the surfactants and residue cleaning agent may require dispersing or solubilizing agents to provide uniform solution concentrates that may be diluted upon use to provide the pretreatment and conditioning. Such solubilizing or dispersing agents may include, but are not limited to, alcohols, glycols, glycerines, and the like. The amount of solubilizing or dispersing agent in the compositions described herein may range from about 2 to about 10 percent by volume based on the total volume of the concentrate.

Other components which may be present in the compositions described herein may include but are not limited to pH adjustment agents, biocides, bacteriacides, sterilization agents, antifungal agents, germicides, dyes, chelating agents, and the like.

The major components of the compositions described herein may promote a pH that is slightly acidic to neutral. However, the compositions may be more effective for the automatic washing machines used in hospitals if the compositions are slightly alkaline. According, a pH adjustment agent may be added to the composition to provide a pH in the range of from about 6.5 to about 10.0. A more desirable pH of the compositions described herein may range from about 8.5 to about 9.5.

A suitable pH adjustment agent may be selected from weak bases such as, ammonium hydroxide, 2-aminopropanoic acid, ammonia, magnesium hydroxide, methylamine, ethylamine, dimethylamine, trimethylamine, pyridine, glycine, hydrazine, and the like. Accordingly, compositions as describe herein may include from about 0.01 to about 1.0 percent by weight of the pH adjustment agent based on a total weight of the composition. Washing solution concentrates may contain from about 0.01 to about 0.5 weight percent of the pH adjustment agent.

The compositions described herein may be particularly suitable for use in an automatic washing and/or disinfection machine used in hospitals to clean medical instruments that have been previously hand washed with other cleaning agents. The low or no foaming tendencies of the compositions make them particularly suitable for such spray washing applications. Other uses of the compositions described herein may include cleaning other surfaces and devices that have been initially cleaned with enzyme cleaning agents.

Once the surfaces of the instruments and devices are clean, the composition described herein may be readily rinsed from the surfaces of the devices so as to leave substantially no visually detectable composition residue or organic material on the surfaces.

An advantage of the compositions described herein is the compositions do not require the addition of antifoam agents. A residual cleaning agent such as SLS tends to foam excessively under turbulent conditions in an aqueous stream. However, use of a sufficient amount of surfactant having an initial Ross-Miles foam height in an aqueous solution at 25° C. of less than 10 millimeters provides sufficient foam inhibition in a turbulent aqueous stream. Accordingly, the combination of residual cleaning agent and surfactant may be used in a flowing stream under extremely turbulent conditions, with or without spray nozzles without excessive foam generation enabling the composition to be turbulently sprayed into an automatic washing machine or used with other high pressure washing systems.

With regard to compositions containing the residual cleaning agent (RCA) and the surfactant component described above, the ranges listed, in Table 1 may be used in automatic washing machines for medical facilities. Higher ratios of RCA to surfactant (Compositions 1-4) may be used where the generation of foam are minimal. By contrast, Compositions 6-10 may be used where turbulence and foaming are problematic with regard to adequate cleaning. For example, Composition 1 having a weight ratio of RCA to surfactant of about 2.7:1 on a 100 wt. % active basis may be injected into an automatic washing machine that is used without first hand washing or rinsing of the medical instruments. Composition 10, having a weight ratio of RCA to surfactant of about 0.016:1 on a 100 wt. % active basis, may be used in automatic washing machines to clean surfaces containing dried blood or other medical waste materials such as ocular fluids and the like subsequent to hand, washing the medical instruments.

Selection of compositions between Compositions 1 and 10 may be made for particular applications depending on washing conditions, size of the automatic washing machines and other factors of machine design that may cause foaming in the washing machine.

TABLE 1

| Composition | Residual Cleaning Agent Solution (RCA), 30 wt. % active | Surfactant, 100 wt. % active | RCA (100 wt. % active)/ Surfactant (100 wt. % active) |
|---|---|---|---|
| 1 | 90 | 10 | 2.7 |
| 2 | 80 | 20 | 1.2 |
| 3 | 70 | 30 | 0.7 |
| 4 | 60 | 40 | 0.45 |
| 5 | 50 | 50 | 0.3 |
| 6 | 40 | 60 | 0.2 |
| 7 | 30 | 70 | 0.128 |
| 8 | 20 | 80 | 0.075 |
| 9 | 10 | 90 | 0.033 |
| 10 | 5 | 95 | 0.016 |

Compositions 1-10 may be diluted in water or a saline solution before use of the compositions in an automatic washing machine, in the table, all weights are in grams of ingredients.

TABLE 2

Composition Formulations Component gram weight additions for each total Solution Concentration Level Percentage

| | 0.25% | | 0.50% | | 1.00% | | 2.00% | |
|---|---|---|---|---|---|---|---|---|
| Comp. | SLS, 30 wt. % active | Non-Ionic Surfactant | SLS, 30 wt. % active | Non-Ionic Surfactant | SLS, 30 wt. % active | Non-Ionic Surfactant | SLS, 30 wt. % active | Non-Ionic Surfactant |
| 1 | 1.0215 | 0.1135 | 2.0430 | 0.2270 | 4.0860 | 0.4540 | 8.1720 | 0.9080 |
| 2 | 0.9080 | 0.2270 | 1.8160 | 0.4540 | 3.6320 | 0.9080 | 7.2640 | 1.8160 |
| 3 | 0.7945 | 0.3405 | 1.5890 | 0.6810 | 3.1780 | 1.3620 | 6.3560 | 2.7240 |
| 4 | 0.6810 | 0.4540 | 1.3620 | 0.9080 | 2.7240 | 1.8160 | 5.4480 | 3.6320 |
| 5 | 0.5675 | 0.5675 | 1.1350 | 1.1350 | 2.2700 | 2.2700 | 4.5400 | 4.5400 |
| 6 | 0.4540 | 0.6810 | 0.9080 | 1.3620 | 1.8160 | 2.7240 | 3.6320 | 5.4480 |
| 7 | 0.3405 | 0.7945 | 0.6810 | 1.5890 | 1.3620 | 3.1780 | 2.7240 | 6.3560 |
| 8 | 0.2270 | 0.9080 | 0.4540 | 1.8160 | 0.9080 | 3.6320 | 1.8160 | 7.2640 |
| 9 | 0.1135 | 1.0215 | 0.2270 | 2.0430 | 0.4540 | 4.0860 | 0.9080 | 8.1720 |
| 10 | 0.0568 | 1.0783 | 0.1135 | 2.1565 | 0.2270 | 4.3130 | 0.4540 | 8.6260 |

| | 4.00% | | 6.00% | | 8.00% | | 10.00% | |
|---|---|---|---|---|---|---|---|---|
| Comp. | SLS, 30 wt. % active | Non-Ionic Surfactant | SLS, 30 wt. % active | Non-Ionic Surfactant | SLS, 30 wt. %, active | Non-Ionic Surfactant | SLS, 30 wt. % active | Non-Ionic Surfactant |
| 1 | 16.3440 | 1.8160 | 24.5160 | 2.7240 | 32.6880 | 3.6320 | 40.8600 | 4.5400 |
| 2 | 14.5280 | 3.6320 | 21.7920 | 5.4480 | 29.0560 | 7.2640 | 36.3200 | 9.0800 |
| 3 | 12.7120 | 5.4480 | 19.0680 | 8.1720 | 25.4240 | 10.8960 | 31.7800 | 13.6200 |
| 4 | 10.8960 | 7.2640 | 16.3440 | 10.8960 | 21.7920 | 14.5280 | 27.2400 | 18.1600 |
| 5 | 9.0800 | 9.0800 | 13.6200 | 13.6200 | 18.1600 | 18.1600 | 22.7000 | 22.7000 |
| 6 | 7.2640 | 10.8960 | 10.8960 | 16.3440 | 14.5280 | 21.7920 | 18.1600 | 27.2400 |
| 7 | 5.4480 | 12.7120 | 8.1720 | 19.0680 | 10.8960 | 25.4240 | 13.6200 | 31.7800 |
| 8 | 3.6320 | 14.5280 | 5.4480 | 21.7920 | 7.2640 | 29.0560 | 9.0800 | 36.3200 |
| 9 | 1.8160 | 16.3440 | 2.7240 | 24.5160 | 3.6320 | 32.6880 | 4.5400 | 40.8600 |
| 10 | 0.9080 | 17.2520 | 1.3620 | 25.8780 | 1.8160 | 34.5040 | 2.2700 | 43.1300 |

With regard to Table 2, generally useful compositions for a wide variety of applications may fall within Compositions 3-5 over a range of dilution of 0.25 to 10% by weight. Other useful compositions may fall within Compositions 8-10 over a range of dilution of 0.25 to 10% by weight. The actual weight percent of active ingredient on 100 wt. % basis for each of the formulations shown in Table 2 may be determined by multiplying the amount of SLS by 0.30, adding the amount of surfactant and dividing the sum by the total weight of SLS, surfactant, and diluent.

It is contemplated, and will be apparent to those skilled in the art from the preceding description that modifications and/or changes may be made in the embodiments of the disclosure. Accordingly, it is expressly intended that the foregoing description is illustrative of exemplary embodiments only, not limiting thereto, and that the true spirit and scope of the present disclosure be determined by reference to the appended claims.

The invention claimed is:

1. A method for cleaning waste treatment system components, medical instruments surfaces or enzyme residue-containing surfaces comprising:
   applying to a surface to be cleaned a composition devoid of an antifoam agent and enzymatic cleaning agent comprising (A) a residue cleaning agent selected from the group consisting of sodium lauryl sulfate, sodium lauryl ether sulfate, ammonium lauryl sulfate, ammonium lauryl ether sulfate, sophorose biosurfactant, sodium lauroyl sarcosinate, triethanolamine lauroyl-L-glutamate, sodium myristyl sarcosinate, sodium dodecyl sulfate, potassium laurate, sodium dodecane sulfonates, and sodium lauryl ethoxysulfate and (B) a substantially non-water soluble nonionic surfactant having an initial Ross-Miles foam height in an aqueous solution at 25° C. of less than 10 millimeters, wherein a weight ratio of residue cleaning agent to surfactant on 100 wt. % active ingredient basis ranges from about 0.05:1 to about 0.5:1, wherein the amount of composition sprayed onto the surface is sufficient to effectively clean and remove residue from the surface; and
   rinsing the surface with purified water to remove the composition from the cleaned surface.

2. The method of claim 1, wherein the weight ratio of residue cleaning agent to surfactant in the composition on 100 wt. % active ingredient basis ranges from about 0.075:1 to about 0.3:1.

3. The method of claim 1 wherein the surfactant comprises a polyether polyol non-ionic surfactant having an initial Ross-Miles foam height in an aqueous solution at 25° C. of less than 5 millimeters.

4. The method of claim 1, wherein the composition has a total active ingredient concentration ranging from about 0.25 wt. % to about 10 wt. %.

5. The method of claim 1, wherein the composition has a total active ingredient concentration ranging from about 0.5 wt. % to about 5 wt. %.

6. A method for removing enzyme residue from enzyme residue-containing surfaces comprising:
   applying to a surface to be cleaned a composition devoid of an antifoam agent and enzymatic cleaning agent comprising (A) a residue cleaning agent selected from the group consisting of sodium lauryl sulfate, sodium lauryl ether sulfate, ammonium lauryl sulfate, ammonium lauryl ether sulfate, sophorose biosurfactant, sodium lauroyl sarcosinate, triethanolamine lauroyl-L-glutamate, sodium myristyl sarcosinate, sodium dodecyl sulfate, potassium laurate, sodium dodecane sulfonates, and sodium lauryl ethoxysulfate and (B) a substantially non-water soluble nonionic surfactant having an initial Ross-Miles foam height in an aqueous solution at 25° C. of less than 10 millimeters, wherein a weight ratio of residue cleaning agent to surfactant on 100 wt. % active ingredient basis ranges from about 0.05:1 to about 0.5:1, wherein the amount of composition sprayed onto the surface is sufficient to effectively clean and remove residue from the surface; and
   rinsing the surface with purified water to remove the composition from the cleaned surface.

7. The method of claim 6, wherein the weight ratio of residue cleaning agent to surfactant in the composition on 100 wt. % active ingredient basis ranges from about 0.075:1 to about 0.3:1.

8. The method of claim 6 wherein the surfactant comprises a polyether polyol non-ionic surfactant having an initial Ross-Miles foam height in an aqueous solution at 25° C. of less than 5 millimeters.

9. The method of claim 6, wherein the composition has a total active ingredient concentration ranging from about 0.25 wt. % to about 10 wt. %.

10. The method of claim 6, wherein the composition has a total active ingredient concentration ranging from about 0.5 wt. % to about 5 wt. %.

* * * * *